(12) United States Patent
Kim et al.

(10) Patent No.: US 11,084,805 B2
(45) Date of Patent: Aug. 10, 2021

(54) COMPOUND DERIVED FROM ALLULOSE

(71) Applicant: CJ CHEILJEDANG CORPORATION, Seoul (KR)

(72) Inventors: Min Hoe Kim, Incheon (KR); Young Mi Lee, Suwon-si (KR); In Sung Kang, Daejeon (KR); Seong Bo Kim, Seongnam-si (KR); Taek Beom Kim, Goyang-si (KR); Sung Bae Byun, Sejong-si (KR); Eun Jung Choi, Seongnam-si (KR); Jong Min Choi, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/491,486

(22) PCT Filed: Aug. 2, 2019

(86) PCT No.: PCT/KR2019/009666
§ 371 (c)(1),
(2) Date: Sep. 5, 2019

(87) PCT Pub. No.: WO2020/189859
PCT Pub. Date: Sep. 24, 2020

(65) Prior Publication Data
US 2020/0377488 A1    Dec. 3, 2020

(30) Foreign Application Priority Data
Mar. 21, 2019 (KR) .......................... 10-2019-0032093

(51) Int. Cl.
*C07D 407/12* (2006.01)

(52) U.S. Cl.
CPC .................................. *C07D 407/12* (2013.01)

(58) Field of Classification Search
CPC ...................................................... C07D 407/12
USPC ......................................................... 514/450
See application file for complete search history.

(56) References Cited

FOREIGN PATENT DOCUMENTS

| | | |
|---|---|---|
| JP | 2000-247991 A | 9/2000 |
| JP | 2006-169124 A | 6/2006 |
| JP | 2008-290995 A | 12/2008 |
| JP | 2011-037821 A | 2/2011 |
| JP | 2012-067028 A | 4/2012 |
| KR | 2017-0105441 A | 9/2017 |
| WO | 2018/127669 A1 | 7/2018 |

OTHER PUBLICATIONS

Matsuo et al., "Dietary D-psicose, a C-3 epimer of D-fructose, suppresses the activity of hepatic lipogenic enzymes in rats," *Asia Pacific J Clin Nutr* 10(3):233-237 (2001).
Matsuo et al., "D-Psicose, a rare sugar that provides no energy and additionally beneficial effects for clinical nutrition," *Asia Pacific Journal of Clinical Nutrition* 13(Suppl):S127 (1 page) (2004).
Okada et al., "Novel fructopyranose oligosaccharides isolated from fermented beverage of plant extract," *Carbohydrate Research* 345:414-418 (2010).
Okada et al., "Isolation and structural confirmation of the oligosaccharides containing α-D-fructofuranoside linkages isolated from fermented beverage of plant extracts," *Carbohydrate Research* 346:2633-2637 (2011).

*Primary Examiner* — Kahsay Habte
(74) *Attorney, Agent, or Firm* — Seed IP Law Group LLP

(57) ABSTRACT

Provided is a novel compound derived from allulose and a composition comprising the same and having acid resistance.

6 Claims, 4 Drawing Sheets

[FIG. 1]
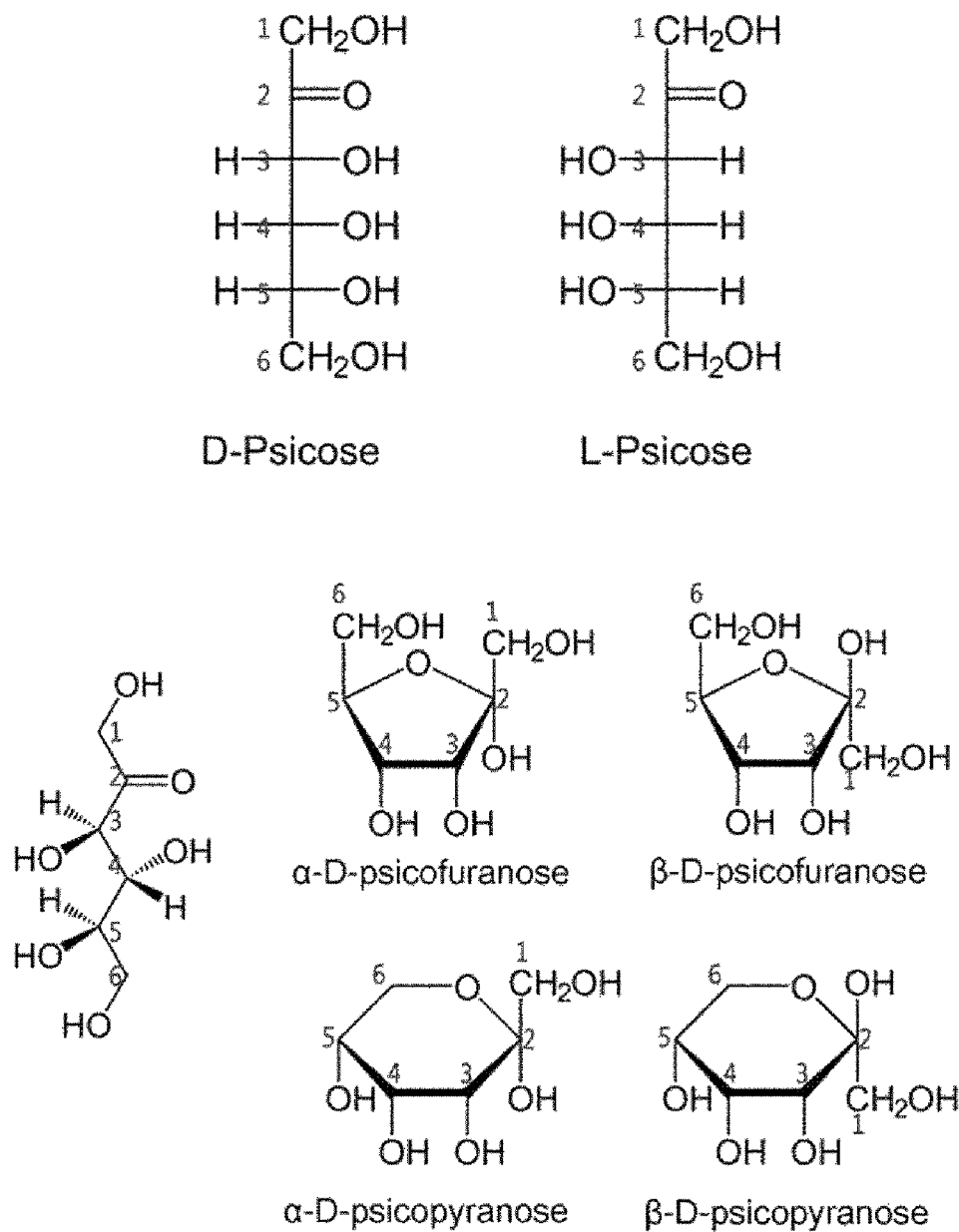

[FIG. 2]
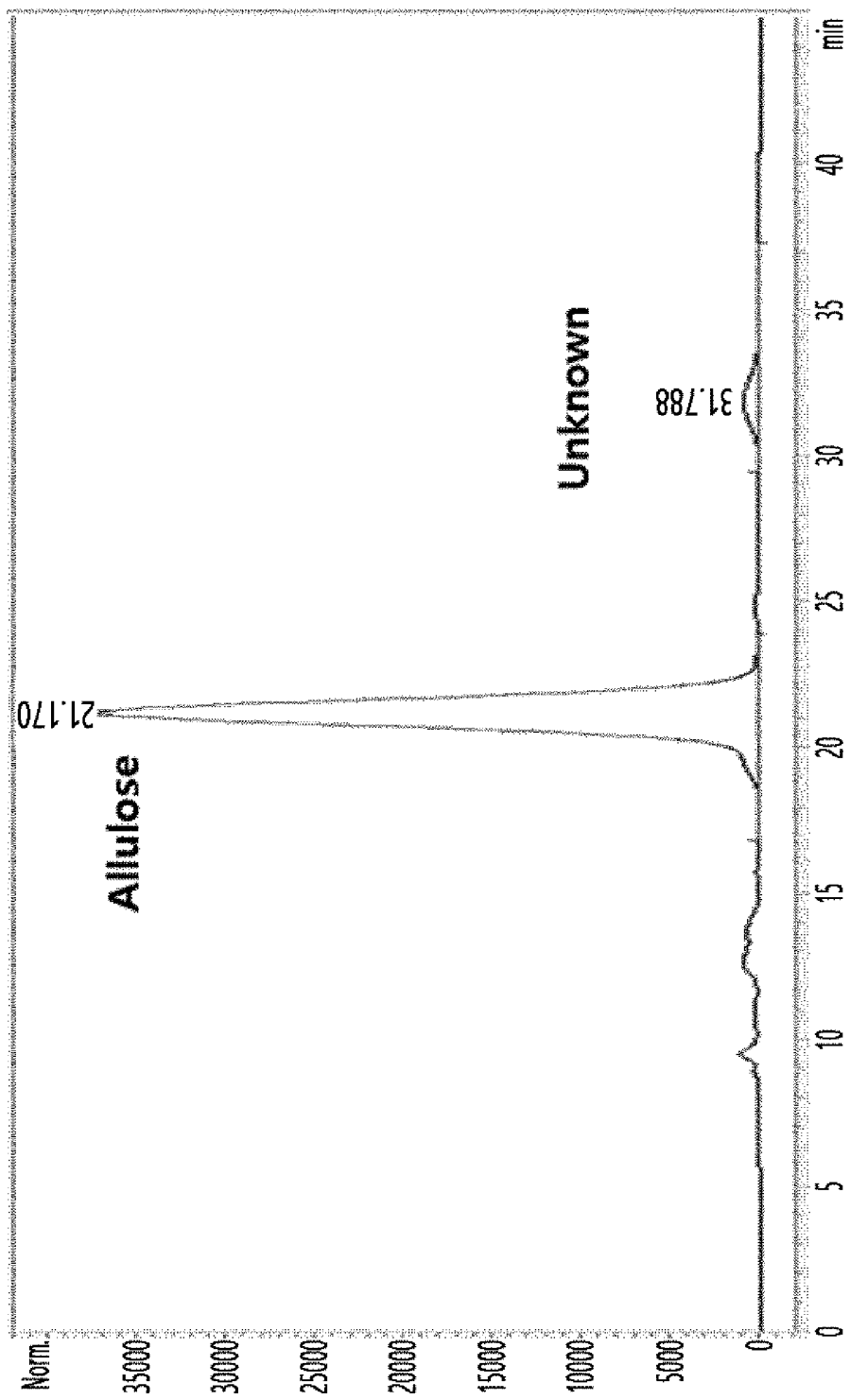

[FIG. 3]
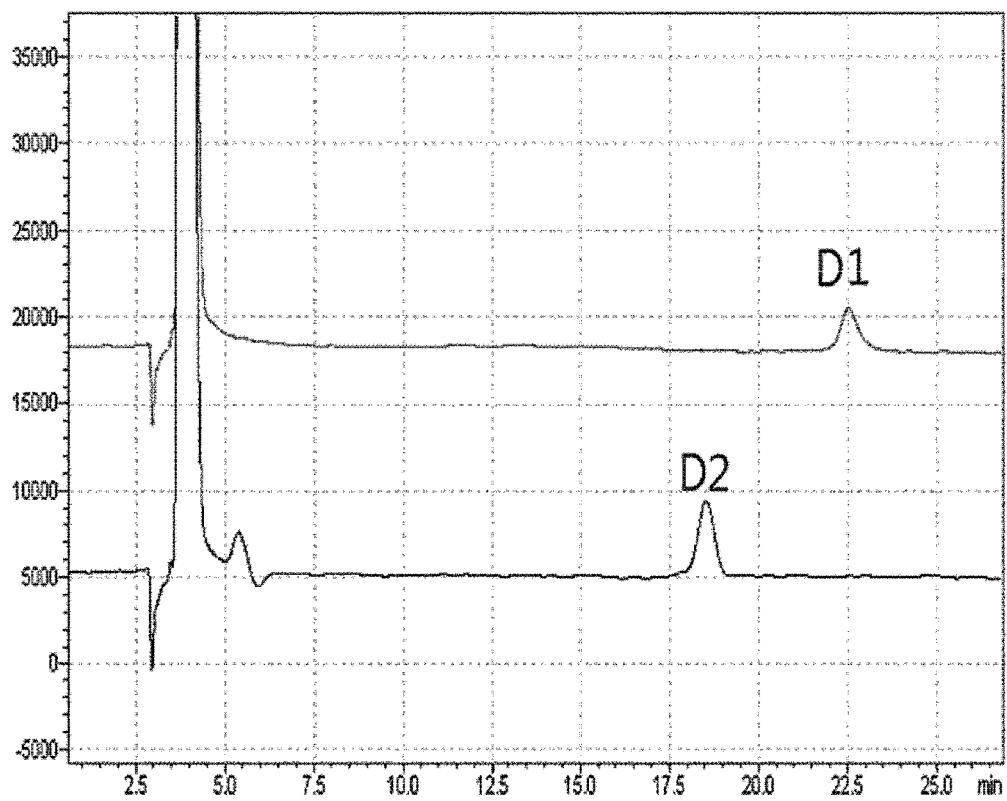

[FIG. 4]
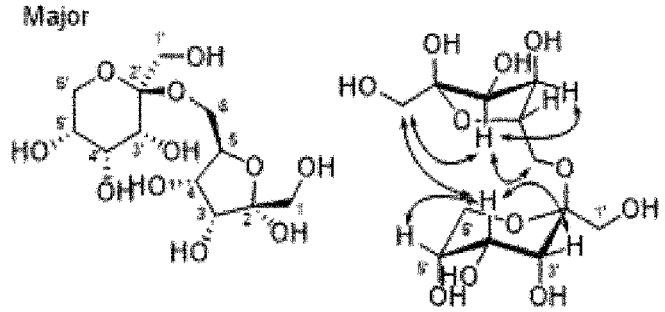
6-O-β-D-Psicopyranosyl-α-D-psicofuranose
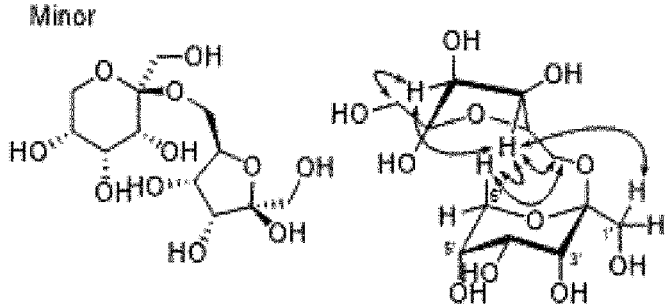
6-O-β-D-Psicopyranosyl-β-D-psicofuranose

COMPOUND DERIVED FROM ALLULOSE

TECHNICAL FIELD

The present disclosure relates to a novel compound derived from allulose and an allulose composition comprising the compound and having acid resistance.

BACKGROUND ART

Allulose, a natural saccharide present in trace amounts in molasses, raisins, figs, and the like, is a monosaccharide with a sweetness of about 70% of sucrose. It has been reported that allulose, unlike fructose or sucrose, is not metabolized in human bodies producing almost no calories and has an effect of inhibiting formation of body fat (Matuo, T. et. al., Asia Pac. J. Clin. Nutr., 10, 233-23; Matsuo, T. and K. Izumori, Asia Pac. J. Clin. Nutr., 13, S127, 2004). Also, since allulose does not affect blood glucose level and non-carious and anticaries functions thereof have been reported, much attention has been paid to allulose as a sugar substitute.

Meanwhile, it has been reported that substances derived from allulose may be limitedly identified by gas chromatography (GC) (WO2018/127669). However, such allulose-derived substances are not separated by liquid chromatography (LC), and thus it is difficult to identify specific properties thereof.

DESCRIPTION OF EMBODIMENTS

Technical Problem

As a result of intensive researches on novel substances derived from allulose, the present inventors have isolated a novel allulose disaccharide generated during allulose manufacturing process and found that the novel disaccharide has acid resistance higher than that of existing disaccharides, thereby completing the present disclosure.

Solution to Problem

An object of the present disclosure is to provide a compound comprising two allulose molecules linked by a glycosidic bond.

Another object of the present disclosure is to provide an allulose composition comprising the compound and monosaccharide allulose and having acid resistance.

Another object of the present disclosure is to provide a composition for a food additive comprising the compound.

Advantageous Effects of Disclosure

A novel allulose disaccharide according to the present disclosure has higher acid resistance than that of sucrose which is an isomer of the allulose disaccharide, and thus may be used not only in food compositions as a sugar substitute but also in various industrial fields.

BRIEF DESCRIPTION OF DRAWINGS

FIG. 1 illustrates structures of allulose and numbered carbon atoms thereof.

FIG. 2 is an HPLC chromatogram of a disaccharide generated during allulose manufacturing process analyzed by a column (Biorad Aminex HPX-87C).

FIG. 3 is an HPLC chromatogram of D1 and D2 obtained by analyzing a substance in a mixture form obtained from the disaccharide generated during allulose manufacturing process using a column (YMC Pack Polyamine II).

FIG. 4 is a stereoscopic structure of D1, as an allulose disaccharide having excellent acid resistance.

BEST MODE

Hereinafter, the present disclosure will be described in detail. Meanwhile, each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed descriptions provided below.

Those skilled in the art will recognize, or be able to ascertain, using no more than routine experimentation, many equivalents to specific embodiments of the present disclosure. Such equivalents are intended to be encompassed in the scope of the following claims.

It is an aspect of the present disclosure to provide a compound comprising two allulose molecules linked by a glycosidic bond.

As used herein, the term "allulose", also known as "psicose", refers to a C-3 epimer of fructose that is a kind of ketohexose.

The allulose molecule according to the present disclosure may have a linear or cyclic structure, and carbon atoms may be numbered consecutively from a carbon atom adjacent to a ketone such that a carbon atom with a ketone group is called C2 according to a method known in the art. According to an embodiment, carbon atoms of allulose according to the present disclosure may be numbered as illustrated in FIG. 1.

Allulose according to the present disclosure may be extracted from natural products or prepared by chemical synthesis methods or biological methods using enzymes, but methods of obtaining allulose are not limited thereto.

Allulose according to the present disclosure may exist as either D- or L-form, e.g., both of the allulose molecules may exist as either D- or L- form, or one of the allulose molecules may exist as D-form and the other may exist as L-form.

An allulose molecule in a state, not linked to another allulose molecule or another saccharide, may be termed "monosaccharide allulose", "allulose monosaccharide", "allulose simple sugar", or "allulose", without being limited thereto.

As used herein, the term "glycosidic bond" refers to an ether bond formed between a hem iacetal hydroxyl group of a saccharide and a functional group of an alcohol, a phenol, a carboxyl, an aldehyde, or the like, specifically, a bond used to join two monosaccharide molecules into a disaccharide.

The term "compound comprising two allulose molecules linked by a glycosidic bond" as used herein may be interchangeably used with terms "allulose disaccharide", "allulose dimer", "disaccharide allulose", and the like.

Particularly, the allulose disaccharide may be a compound comprising two allulose molecules, one of which is a cyclic allulose, linked by a glycosidic bond formed between a hydroxyl group at position 2 of the cyclic allulose and a hydroxyl group at position 1 to 6 of the other allulose molecule. One or two glycosidic bonds may be formed, specifically, one glycosidic bond may be formed.

According to an embodiment, the glycosidic bond may be a glycosidic bond formed between a hydroxyl group at position 2 of one cyclic allulose and a hydroxyl group at position 6 of the other allulose.

According to an embodiment, one of the two allulose molecules is in the form of psicofuranose and the other allulose molecule is in the form of psicopyranose, and the allulose disaccharide may be represented by Formula 1 below, without being limited thereto.

Formula 1

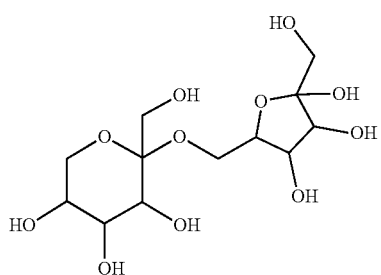

According to an embodiment, the allulose disaccharide may be represented by Formula 2 below, without being limited thereto.

Formula 2

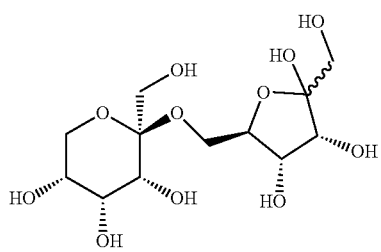

According to an embodiment, the allulose disaccharide of the present disclosure may be a compound named 2-(hydroxymethyl)-2-((3,4,5-trihydroxy-5-(hydroxymethyl)tetrahydrofuran-2-yl)methoxy)tetrahydro-2H-pyran-3,4,5-triol, more specifically, (2S,3R,4R,5R)-2-(hydroxymethyl)-2-(((2R,3S,4R)-3,4,5-trihydroxy-5-(hydroxymethyl) tetrahydrofuran-2-yl)methoxy)tetrahydro-2H-pyran-3,4,5-triol, without being limited thereto.

The (2S,3R,4R,5R)-2-(hydroxymethyl)-2-(((2R,3S,4R)-3,4,5-trihydroxy-5-(hydroxymethyl) tetrahydrofuran-2-yl)methoxy)tetrahydro-2H-pyran-3,4,5-triol may collectively refer to compounds named 6-O-β-D-psicopyranosyl-α-D-psicofuranose or 6-O-β-D-psicopyranosyl-β-D-psicofuranose, according to the form of psicofuranose. Specifically, a structure of 6-O-β-D-psicopyranosyl-α-D-psicofuranose may be represented by Formula 3 below, and a structure of 6-O-β-D-psicopyranosyl-β-D-psicofuranose may be represented by Formula 4 below.

Formula 3

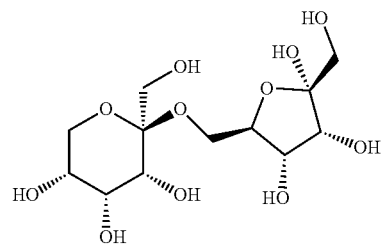

Formula 4

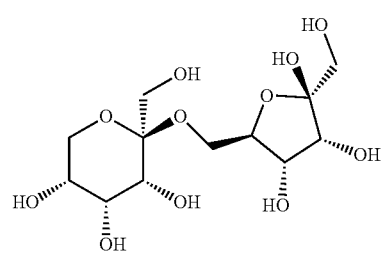

Also, the (2S,3R,4R,5R)-2-(hydroxymethyl)-2-(((2R,3S,4R)-3,4,5-trihydroxy-5-(hydroxymethyl) tetrahydrofuran-2-yl)methoxy)tetrahydro-2H-pyran-3,4,5-triol, may be, but is not limited to, a compound named (2S,3R,4R,5R)-2-(hydroxymethyl)-2-(((2R,3S,4R,5S)-3,4,5-trihydroxy-5-(hydroxymethyl)tetrahydrofuran-2-yl)methoxy)tetrahydro-2H-pyran-3,4,5-triol, or a compound named (2S,3R,4R,5R)-2-(hydroxymethyl)-2-(((2R,3S,4R,5R)-3,4,5-trihydroxy-5-(hydroxymethyl)tetrahydrofuran-2-yl)methoxy)tetrahydro-2H-pyran-3,4, 5-triol.

The compound of the present disclosure may have acid resistance.

As used herein, the term "acid resistance" refers to stability against acid. Specifically, acid resistance in the present disclosure may mean the ability of a certain compound to maintain inherent properties thereof without losing the properties against acid, and more specifically, the compound having acid resistance in the present disclosure may refer to a compound having acid resistance similar to or higher than that of other disaccharides, without being limited thereto. According to an embodiment, the compound having acid resistance may be any compound having higher acid resistance than that of an isomer thereof, specifically, higher acid resistance than that of sucrose, without being limited thereto. The acid resistance may be evaluated by storing a compound in an acidic environment, specifically exposing the compound to an environment of pH 7 or less, for more than 0 hour, and measuring residual amounts of the compound by measuring changes in purity, mass, weight, and the like with time, without being limited thereto.

The compound of the present disclosure may have acid resistance at pH 0.1 to pH 7, and more specifically, at pH 0.5 to pH 7, pH 0.7 to pH 7, pH 1 to pH 7, pH 1 to pH 6.7, pH 1 to pH 6.5, pH 1.5 to pH 6.5, pH 1.5 to pH 6, pH 2 to pH 6, pH 2 to pH 5.5, pH 2 to pH 5, pH 2 to pH 4.5, or pH 2 to pH 4, without being limited thereto.

In addition, the residual amount of the compound according to the present disclosure, when stored at pH 2 to pH 7 for 0 hour to 120 hours, may be 40 parts by weight or more, specifically 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98 parts by weight or more, more specifically, 99 parts by weight or more, based on 100 parts by weight of an initial amount, and the storage time may be 120 hours or more, 96 hours or more, 84 hours or more, 72 hours or more, 60 hours or more, 48 hours or more, 36 hours or more, 24 hours or more, 12 hours or more, or 6 hours or more, without being limited thereto.

It is another aspect of the present disclosure to provide a saccharide composition comprising the allulose disaccharide according to the present disclosure and a monosaccharide allulose.

In the composition, the allulose disaccharide may be contained in an amount greater than 0 part by weight and 20 parts by weight or less based on 100 parts by weight of a total weight of the allulose disaccharide and the monosaccharide allulose, specifically, in an amount of 15 parts by weight or less, 13 parts by weight or less, 11 parts by weight or less, 10 parts by weight or less, 9 parts by weight or less, 8 parts by weight or less, 7 parts by weight or less, 6 parts by weight or less, 5 parts by weight or less, 4 parts by weight or less, 3 parts by weight or less, 2.5 parts by weight or less, 2 parts by weight or less, 1.5 parts by weight or less, 1 part by weight or less, 0.7 parts by weight or less, 0.6 parts by weight or less, 0.5 parts by weight or less, 0.4 parts by weight or less, 0.3 parts by weight or less, 0.2 parts by weight or less, 0.1 parts by weight or less, 0.0001 parts by weight or less, or 0.001 parts by weight or less and/or greater than 0 part by weight, 0.1 parts by weight or more, 0.5 parts by weight or more, 0.7 parts by weight or more, 1 part by weight or more, 1.5 parts by weight or more, 2 parts by weight or more, or 3 parts by weight or more, without being limited thereto.

In addition, the composition of the present disclosure may exist in a crystalline or liquid form. In accordance with the form, the amount of the allulose disaccharide may vary in the composition. Specifically, when the composition of the present disclosure is in the crystalline form, the amount of the allulose disaccharide contained in the composition may be 5 parts by weight or less, 4 parts by weight or less, 3 parts by weight or less, 2.5 parts by weight or less, 2 parts by weight or less, 1.5 parts by weight or less, 1 part by weight or less, 0.7 parts by weight or less, 0.6 parts by weight or less, 0.5 parts by weight or less, 0.4 parts by weight or less, 0.3 parts by weight or less, 0.2 parts by weight or less, 0.1 parts by weight or less, 0.05 parts by weight or less, 0.005 parts by weight or less, 0.001 parts by weight or less, 0.0005 parts by weight or less, or 0.0001 parts by weight or less, and/or greater than 0 part by weight, 0.1 parts by weight or more, 0.5 parts by weight or more, 0.7 parts by weight or more, 1 part by weight or more, 1.5 parts by weight or more, 2 parts by weight or more, or 3 parts by weight or more, based on 100 parts by weight of the total weight of the allulose disaccharide and the allulose monosaccharide, without being limited thereto.

When the composition of the present disclosure is in the liquid form, the amount of the allulose disaccharide contained in the composition may be 15 parts by weight or less, 13 parts by weight or less, 11 parts by weight or less, 10 parts by weight or less, 9 parts by weight or less, 8 parts by weight or less, 7 parts by weight or less, 6 parts by weight or less, 5 parts by weight or less, 4 parts by weight or less, 3 parts by weight or less, 2.5 parts by weight or less, 2 parts by weight or less, 1.5 parts by weight or less, 1 part by weight or less, 0.7 parts by weight or less, 0.6 parts by weight or less, 0.5 parts by weight or less, 0.3 parts by weight or less, 0.2 parts by weight or less, 0.1 parts by weight or less, 0.05 parts by weight or less, 0.005 parts by weight or less, 0.001 parts by weight or less, 0.0005 parts by weight or less, or 0.0001 parts by weight or less, and/or greater than 0 part by weight, 0.1 parts by weight or more, 0.5 parts by weight or more, 0.7 parts by weight or more, 1 part by weight or more, 1.5 parts by weight or more, 2 parts by weight or more, or 3 parts by weight or more, based on 100 parts by weight of the total weight of the allulose disaccharide and the allulose monosaccharide, without being limited thereto.

It is another aspect of the present disclosure to provide a food composition comprising the allulose disaccharide according to the present disclosure.

The food composition according to the present disclosure may include general foods, health foods, and medicinal (or patient) food compositions, without being limited thereto. Specifically, the food composition according to the present disclosure may be a beverage (e.g., dietary fiber drink, carbonated water, and baked flour soup, tea), an alcohol drink, a bakery product, a sauce (e.g., ketchup and BBQ sauce), a dairy product (e.g., fermented milk), a processed meat (e.g., ham and sausage), a chocolate confectionary, a gum, a candy, a jelly, an ice cream, a syrup, a dressing, a snack (e.g., cookie and cracker), a fruit conserve (e.g., fruit preparation, glace fruit, red ginseng juice, or sliced red ginseng), a meal substitution food (e.g., frozen food and home meal replacement (HMR)), or a processed food. More specifically, the food composition may be a carbonated beverage composition, without being limited thereto.

When the allulose disaccharide according to the present disclosure is used in the food composition, the sweetener according to the present disclosure may be used alone or in combination with other ingredients, and may be appropriately used according to any method commonly used in the art. The food composition according to the present disclosure may further contain various flavoring agents or natural carbohydrates as additional ingredients. Examples of the natural carbohydrates may include monosaccharides such as glucose and fructose, disaccharides such as maltose and sucrose, polysaccharides such as dextrin and cyclodextrin, and sugar alcohols such as xylitol, sorbitol and erythritol. As a sweetener, a natural sweetener such as thaumatin and stevia extract and a synthetic sweetener such as saccharin and aspartame may be used.

In addition to the ingredients described above, the food composition according to the present disclosure may further contain various nutritional supplements, vitamins, minerals, flavors, colorants, pectin and salts thereof, alginic acid and salts thereof, organic acids, protective colloid thickeners, pH adjusters, stabilizers, preservatives, glycerin, alcohols, carbonating agents used in carbonated drinks, and the like. Also, the food composition according to the present disclosure may contain flash of fruits or vegetables for natural fruit juices, fruit juice beverages and vegetable drinks. These ingredients may be used alone or in combination thereof. These additional ingredients may be contained in the food composition according to the present disclosure in an amount of 0.01 parts by weight to 0.20 parts by weight based on 100 parts by weight of the food composition.

The novel compound derived from allulose according to the present disclosure may be used in the form of a sitologically acceptable salt.

As used herein, the term "sitologically acceptable salt" may be used interchangeably with "pharmaceutically acceptable salt" and refers to a formulation which does not cause serious stimulation in an organism into which the compound is administered and does not deteriorate biological activities and physical properties of the compound. The salt may refer to any salt which has desired biological or physiological activities of the compound or derivatives thereof and exhibits minimum undesired toxicological effects. According to an embodiment, the salt may be in the form of an acid addition salt formed by a pharmaceutically acceptable free acid. The acid addition salt may be prepared by any method commonly used in the art, for example, by dissolving the compound in an excess amount of an aqueous acid solution followed by precipitation of the salt using a water-miscible organic solvent, e.g., methanol, ethanol, acetone, or acetonitrile. The compound and acid or alcohol in water (e.g., glycol and monomethyl ether) in the same molar amount may be heated and subsequently, the mixture may be dried by evaporation, or precipitated salts may be filtered by suction. In this regard, the free acid may be an inorganic acid or an organic acid. The inorganic acid may be hydrochloric acid, hydrobromic acid, phosphoric acid, nitric acid, sulfuric acid, tartaric acid, or the like, and the organic acid may be methane sulfonic acid, p-toluene sulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, or the like, without being limited thereto.

In addition, a pharmaceutically acceptable metal salt may be prepared by using a base. For example, an alkali metal or alkaline earth metal salt is obtained by dissolving the compound in an excess amount of an alkali metal hydroxide or alkaline earth metal hydroxide solution, filtering a non-soluble compound salt, and then evaporating and drying the filtrate. In this regard, as the metal salt, a sodium salt, a potassium salt, or a calcium salt is preferably prepared from a pharmaceutical aspect, without being limited thereto. In addition, a silver salt corresponding thereto may be obtained by reacting an alkali metal or alkaline earth metal salt with a suitable silver salt (e.g., silver nitrate).

The sitologically acceptable salt according to the present disclosure may include any salt of an acidic or basic group possibly present in the compound, unless otherwise indicated. For example, the sitologically acceptable salt may include sodium, calcium and potassium salts of a hydroxyl group, and other sitologically acceptable salts of an amino group may include hydrobromide, sulfate, hydrosulfate, phosphate, hydrophosphate, dihydrophosphate, acetate, succinate, citrate, tartrate, lactate, mandelate, methane sulfonate (mesylate), and p-toluene sulfonate (tosylate), which may be prepared by any method of preparing salts well known in the art.

MODE OF DISCLOSURE

Hereinafter, the present disclosure will be described in more detail with reference to the following examples and experimental examples. However, these examples and experimental examples are for illustrative purposes only and are not intended to limit the scope of the present disclosure.

EXAMPLE 1

Separation of Novel Allulose Disaccharide

A disaccharide was separated from a solution before crystallization step of allulose by high performance liquid chromatography (HPLC) during allulose manufacturing process disclosed in Korean Patent No. 10-1723007 in a different manner from that disclosed in International Patent Publication No. WO2018/127669. Specifically, it was confirmed that a novel (unknown) substance, in addition to allulose, was generated in the solution before the crystallization step as shown in FIG. 2, by performing HPLC under HPLC analysis conditions listed in Table 1 below.

Although the amount of the novel substance separated as described above slightly varied according to the manufacturing process, it was confirmed that the amount of the novel substance contained in the initial solution was 2% or less and increased to about 5% in accordance with storage time.

TABLE 1

| Equipment | Agilent technologies 1200 series |
|---|---|
| Column | Biorad Aminex HPX-87C |
| | (7.8 × 300 mm, 9 µm) |
| Eluent | Water |
| Flow rate | 0.6 mL/min |
| Temperature | 80° C. |
| RI cell temperature | 35° C. |

As a result, allulose was identified at 21.1 minutes, and the novel substance was identified at 31.7 minutes.

Thus, in order to separate the generated novel substance, the novel substance was purified to a purity of 95% or more by preparative HPLC and precisely separated by a column.

Specifically, HPLC was performed.

Separation conditions for HPLC are as shown in Table 2 below.

TABLE 2

| Equipment | Shimadzu LC 10A |
|---|---|
| Column | YMC Pack Polyamine II |
| | (4.6 × 250 mm, 5 µm, 12 nm) |
| Eluent | Acetonitrile/Water (80/20) |
| Flow rate | 1 mL/min |
| Temperature | 30° C. |
| RI cell temperature | 30° C. |

As a result, it was confirmed that the substances shown as one peak under the HPLC conditions listed in Table 1 were observed as two separate peaks under the separation conditions listed in Table 2 (FIG. 3). One separated substance showing the peak identified at 22.5 minutes was named D1 and the other substance showing the peak identified at 17.7 minutes was named D2.

EXAMPLE 2

Identification of Allulose Disaccharide

D1 identified in Example 1 was further analyzed.

The major component, 6-O-β-D-Psicopyranosyl-α-D-psicofuranose, was white amorphous powder, ES I-MS m/z 365 [M+Na]$^+$; $^1$H NMR (850 MHz, D$_2$O) $\delta_H$ 3.44 (1H, d, J=12.0 Hz), 3.47 (1H, d, J=12.0 Hz), 3.56 (1H, dd, J=11.0, 5.0 Hz), 3.60 (1H, d, J=12.0 Hz), 3.62 (1H, dd, J=11.0, 2.5 Hz), 3.70 (1H, br d, J=12.5 Hz), 3.75 (1H, d, J=12.0 Hz), 3.75 (1H, br m$^a$), 3.82 (1H, br d, J=12.5 Hz), 3.84 (1H, br s), 3.92 (1H, t, J=3.0 Hz), 3.97 (1H, d, J=5.5 Hz), 4.09 (1H, t, J=5.5 Hz), 4.13 (1H, br m) [D$_2$O signal $\delta_H$ 4.70]; $^{13}$C NMR signals$^b$ $\delta_C$ 57.6, 60.4, 62.9, 64.7, 64.9, 69.1, 68.9, 70.2, 70.3, 81.2, 101.8, 103.4.

A. It was difficult to measure spin-spin splitting (multiplicity) and coupling constant due to overlapping of peaks.

B. $^{13}$C NMR peak information was obtained by interpreting HSQC (850 MHz, D$_2$O) and HMBC (850 MHz, D$_2$O) spectral data of NMR The minor component, 6-O-β-D-Psicopyranosyl-β-D-psicofuranose, was white amorphous powder, ES I-MS m/z 365

[M+Na]+; 1H NMR (850 MHz, D$_2$O) δ$_H$ 3.49 (1H, d, J=13.0 Hz), 3.73 (1H, d, J=13.0 Hz), 3.58 (1H, m$^a$), 3.68 (1H, dd, J=11.0, 2.5 Hz), 3.62 (1H, m$^a$), 3.71 (1H, br d, J=12.0 Hz), 3.82 (1H, br d, J=12.0 Hz), 3.76 (1H, br m$^a$), 3.78 (1H, m$^a$), 3.87 (1H, br s), 3.98 (1H, t, J=3.0 Hz), 3.95 (1H, d, J=4.5 Hz), 4.00 (1H, br m), 4.34 (1H, dd, J=8.0, 4.5 Hz) [D$_2$O signal δ$_H$ 4.70]; 13C NMR signals[b] δ$_C$ 57.7, 61.4, 62.2, 64.7, 64.8, 69.0, 69.2, 70.8, 74.4, 80.8, 101.8, 105.9.

A. It was difficult to measure spin-spin splitting (multiplicity) and coupling constant due to overlapping of peaks.

B. 13C NMR peak information was obtained by interpreting HSQC (850 MHz, D$_2$O) and HMBC (850 MHz, D$_2$O) spectral data of NMR.

As a result, it was confirmed that D1 is a novel allulose disaccharide and has a structure of Formula 2 below.

Formula 2

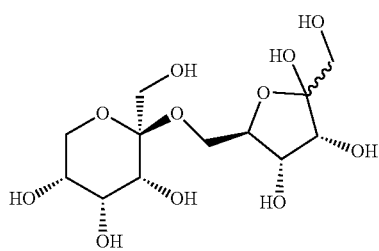

Meanwhile, it was confirmed that D1 has two types of optical isomeric structures. Specifically, it was confirmed that the stereochemistry of carbon at position 2 (at position 5 based on IUPAC name) of the pentagonal ring-shaped D-allulose (D-psicofuranose) was changed in the major/minor form (FIG. 4). That is, it was confirmed that the following Formula 3 corresponds to a major form, and that the following Formula 4 corresponds to a minor form.

Formula 3

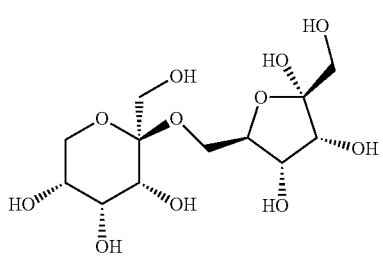

Formula 4

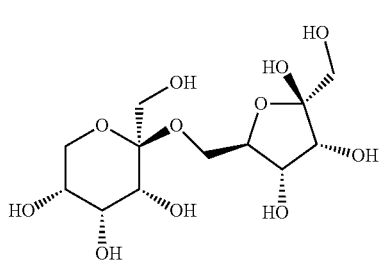

In addition, it was confirmed that D2 is a novel allulose disaccharide as a structural isomer of the compound of Formula 2 in which the hydroxyl group at position 2 of one allulose molecule is linked to the hydroxyl group at position 1 to 6 of the other allulose molecule by a glycosidic bond.

EXAMPLE 3

Evaluation of Acid Resistance of Allulose Disaccharide

1% D1 solution was prepared (in 10 mM citrate buffer) to measure acid resistance thereof. Sucrose that is a disaccharide having a similar structure and D2 that is another allulose disaccharide were used as controls.

The pH of the solution was adjusted to pH 2.0, 4.0, and 6.0 using 10 mM citrate and sodium citrate buffers. The prepared solutions were respectively stored at room temperature (at about 40° C.), and purities of remaining substances were identified by HPLC analysis (HPX-87C column, 80° C., 60 min, 20 μl) at 0 hour, 24 hours, 72 hours, and 120 hours. Residual percentages of D1, D2, and sucrose are shown in Table 3 below. The concentration of each substance was 1% (w/v) and reaction temperature was 40° C.

Those results which show statistically significant difference under the same experimental conditions were indicated by different alphabets.

TABLE 3

| Time (hr) | D1 | D2 | Sucrose | p |
|---|---|---|---|---|
| pH 2, Temperature 40° C. | | | | |
| 0 | 100.0 | 100.0 | 100.0 | — |
| 24 | 85.9$^A$ | 71.1$^C$ | 81.2$^B$ | 0.000 |
| 72 | 58.2$^A$ | 39.5$^C$ | 51.9$^B$ | 0.000 |
| 120 | 44.6$^A$ | 21.2$^C$ | 34.4$^B$ | 0.000 |
| pH 4, Temperature 40° C. | | | | |
| 0 | 100.0 | 100.0 | 100.0 | — |
| 24 | 99.0$^A$ | 98.4$^A$ | 98.1$^A$ | 0.109 |
| 72 | 98.8$^A$ | 95.9$^B$ | 95.8$^B$ | 0.001 |
| 120 | 97.9$^A$ | 93.2$^B$ | 92.9$^B$ | 0.000 |
| pH 6, Temperature 40° C. | | | | |
| 0 | 100.0 | 100.0 | 100.0 | — |
| 24 | 100.0 | 100.0 | 100.0 | 0.781 |
| 72 | 100.0 | 100.0 | 99.9 | 0.397 |
| 120 | 99.96$^{A*}$ | 99.64$^{A*}$ | 99.58$^{A*}$ | 0.069* |

※ Different characters A, B, and C indicate significant differences between results in the horizontal row
※*is p < 0.1, and shows borderline significant trend of D1 and D2 compared with sucrose The measured results with respect to storage time were analyzed using analysis of variance (ANOVA) as statistical analysis and tukey's multiple range test as post hoc analysis, and statistical significance was set to p<0.05.

As a result, it was confirmed that difference in the residual percentages increased as time increased and the pH decreased. Particularly, it was confirmed that the residual percentages of D1 stored in a very strong acid condition of pH 2 after 120 hours was about 130% higher than that of sucrose.

Based on the results, it was confirmed that D1 had higher acid resistance than that of D2 and sucrose, which have similar structures, at pH 6 or less, indicating that disaccharides having similar structures can have different acid resistances and also the novel allulose disaccharide according to the present disclosure has excellent acid resistance.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure should be defined by the appended claims rather than the detailed description, and it should be understood that all modifications or variations derived from the meanings and scope of the present disclosure and equivalents thereof are included in the scope of the present disclosure.

The invention claimed is:

1. A compound in which two molecules of allulose are linked, wherein the compound is 2-(hydroxymethyl)-2-((3,4,5-trihydroxy-5-(hydroxymethyl)tetrahydrofuran-2-yl)methoxy)tetrahydro-2H-pyran-3,4,5-triol, represented by Formula 1 below:

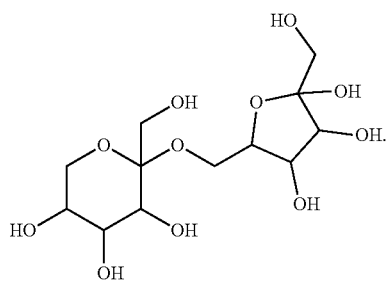

Formula 1

2. The compound according to claim 1, wherein the compound is (2S,3R,4R,5R)-2-(hydroxymethyl)-2-(((2R,3S,4R,5S)-3,4,5-trihydroxy-5-(hydroxymethyl)tetrahydrofuran-2-yl)methoxy)tetrahydro-2H-pyran-3,4,5-triol or (2S,3R,4R,5R)-2-(hydroxymethyl)-2-(((2R,3S,4R,5R)-3,4,5-trihydroxy-5-(hydroxymethyl)tetrahydrofuran-2-yl)methoxy)tetrahydro-2H-pyran-3,4,5-triol.

3. The compound according to claim 1, wherein the compound is represented by Formula 3 or 4 below:

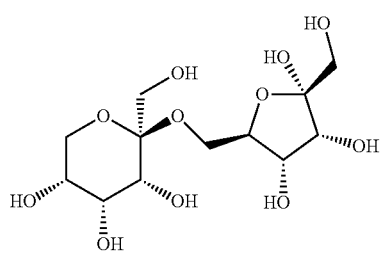

Formula 3

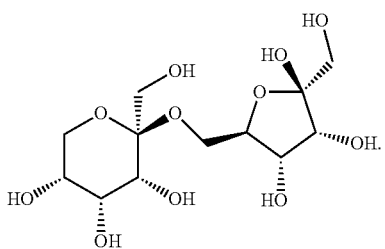

Formula 4

4. The compound according to claim 1, wherein the compound has acid resistance at pH 0.1 to 7.

5. A saccharide composition comprising the compound of claim 1 and a monosaccharide allulose.

6. A composition for a food additive comprising the compound of claim 1.

* * * * *